United States Patent [19]

Hansen

[11] Patent Number: 4,661,451
[45] Date of Patent: Apr. 28, 1987

[54] METHODS FOR IMMOBILIZING AND TRANSLOCATING BIOLOGICAL CELLS

[75] Inventor: W. Peter Hansen, Middleboro, Mass.

[73] Assignee: Ortho Diagnostic Systems, Inc., Raritan, N.J.

[21] Appl. No.: 577,120

[22] Filed: Feb. 6, 1984

[51] Int. Cl.$^4$ ................ C12N 11/00; C12N 11/16; C12N 13/00; C12N 11/14

[52] U.S. Cl. .................. 435/174; 435/173; 435/176; 435/177; 435/178; 435/179; 435/180; 435/181; 435/182; 435/288; 436/63; 436/177; 436/178; 204/403; 204/299 R

[58] Field of Search ............. 435/173, 174, 176–182, 435/288; 424/3; 204/180 R, 299 R, 403; 210/748, 243; 436/63, 177, 178; 422/101; 209/127 R; 219/203, 212

[56] References Cited

U.S. PATENT DOCUMENTS 3,739,142  6/1973  Johns ...................... 219/212
3,895,213  7/1975  Levin ...................... 219/203
4,440,638  4/1984  Judy et al. ................ 210/748

OTHER PUBLICATIONS

Ann. N.Y. Acad. Sciences, 238, 176 (1974), pp. 176–185, Chen et al.
Vien Ken et al., FEBS Letters, vol. 137, No. 1 (1982), pp. 11–13.
Laboratory Equipment Digest, vol. 18, No. 10 (Oct. 1980), pp. 91–93.

*Primary Examiner*—Sidney Marantz
*Assistant Examiner*—Louanne C. Krawczewicz
*Attorney, Agent, or Firm*—Mark A. Hofer

[57] ABSTRACT

Apparatus for immobilizing biological cells based on the dielectric properties of biological cells. An inhomogeneous electric field emanating from a grid point location or other contact area is created and attracts the biological cell into contact therewith. Appropriate controls over a series of grid points permits controlled inter-grid point movement of cells thereby permitting sequential testing or sorting processes to be carried out.

5 Claims, 5 Drawing Figures

METHODS FOR IMMOBILIZING AND TRANSLOCATING BIOLOGICAL CELLS

FIELD OF THE INVENTION

This invention relates to apparatus useful for immobilizing biological cells on a surface and for selectively releasing or imparting predetermined motion to biological cells and is particularly useful in conjunction with the generalized cytometry instrument of the commonly assigned co-pending application of Louis A. Kamentsky entitled "Generalized Cytometry Instrument And Methods Of Use", filed concurrently herewith and having Ser. No. 577,448.

BACKGROUND OF THE INVENTION

In U.S. application Ser. No. 577,448 of Louis A. Kamentsky describing a generalized cytometry instrument, a necessary aspect involves the immobilization of the cells to be examined onto a surface. Kamentsky describes the use of immobilizing media such as agarose for suspending the cells in a fixed position and for providing viable nutrients or reagents to same. Alternately, Kamentsky discloses the use of immobilized antibodies for selectively or nonspecifically securing desired cells to the surface for subsequent illumination, detection, and analysis.

It is an object of the present invention to provide another means whereby biological cells may be immobilized to a surface.

It is a yet further object of the present invention that apparatus and methods be provided for immobilizing biological cells in a manner whereby they may be selectively released for purification procedures and the like in response to detected cellular characteristics.

It is a yet further object of the present invention to provide methods and apparatus which, in conjunction with data results obtained by the generalized cytometry instrument, permit the specified translocation of cells thereby effecting purification and segregation of those cells either desired or undesired from a heterogeneous population.

SUMMARY OF THE INVENTION

In accordance with the principles and objects of the present invention, there are provided apparatus and methods for immobilizing biological cells based upon their dielectric properties in an inhomogeneous or non uniform electric field. Cells, when placed in an inhomogeneous electric field generated by, for instance, an alternating current source, exhibit a net force in the direction of the field's source hereinafter referred to as grid points. By arranging an array of grid points having the numerical density desired to attract and immobilize the number of cells required for analysis in a desired pattern, and by connecting same to an inhomogeneous field generating source, one may vastly simplify cell locating operations such as those performed by Kamentsky's generalized cytometry instrument since the cells' position will now be associated with the grid point locations.

By individually connecting the grid points to controlling means, one may selectively energize grid points or other conducting contact areas and if the inter-grid point distances are appropriately selected and the proper fields applied in a coordinated timing sequence, one may ideally effect a predetermined translocation of the cells. This will advantageously permit the removal of undesired cells by translocating them to "sinks" for disposal and the purification of desired cells by their movement to other predetermined collection locations.

BRIEF DESCRIPTION OF THE DRAWINGS

Further understanding of the invention may be had by reference to the drawings wherein.

DETAILED DESCRIPTION OF THE DRAWINGS AND BEST MODE

Figure 1:
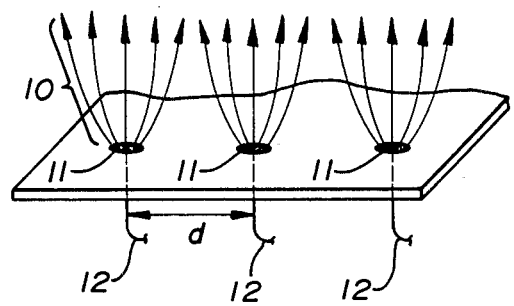
FIG. 1 shows a stylized view of the inhomogeneous fields resulting from energized grid points.

With reference to FIG. 1, there is shown a series of grid points generating an inhomogeneous field graphically depicted by the curving field lines 10 from grid points 11. The inhomogeneous or non uniform field may be advantageously generated by connecting grid points 11 via connections 12 to an alternating current source oscillating in the kilohertz range.

Figure 2:
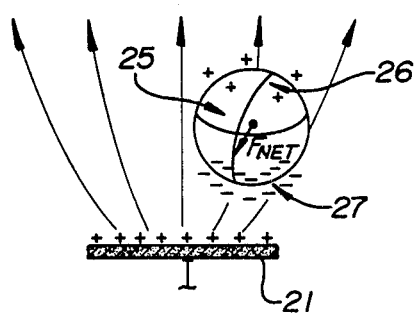
FIG. 2 shows cellular interactions when placed within an inhomogeneous field.

It is well-known that dielectric particles, such as biological cells 25, see FIG. 2, experience a force of attraction in a nonuniform electric field. This force, depicted as $F_{net}$ in FIG. 2, produces motion of the cell in the direction of the highest field strength. As may be readily seen by examination of FIG. 2, the field strength at point 27 is larger than that experienced by the cell at point 26 and accordingly the cellular surface charges are greater at 27 than at 26. Thus, in accordance with the attraction between unlike charges, cell 25 experiences a force $F_{net}$ in a direction of grid point 21.

With appropriate manipulation of the cellular concentration in solution as well as the density of grid points, each grid point will preferably attract on the average one or less cells. At higher cell concentrations, the cells will disadvantageously tend to form chains extending from the location of the grid point toward the region of lowest electric field strength and unless this effect is specifically desired, it is advantageously avoided. Release of the cells from the grid points may be readily accomplished by merely disconnecting the grid point from the current source thereby turning off the electric field and eliminating the grid point's attractive influence upon the cell.

It should be noted that, in accordance with the types of cells to be immobilized, the suspending solution must be appropriately adjusted to permit the generation of the inhomogeneous electric field. It will ideally also be chosen to provide an environment suitable for continued or maintaining cellular viability for a time at least sufficient to conduct the desired testing or culturing of the cells, particularly if it is to be employed with the class of generalized cytometry instruments such as those described by Kamentsky.

Figure 3:
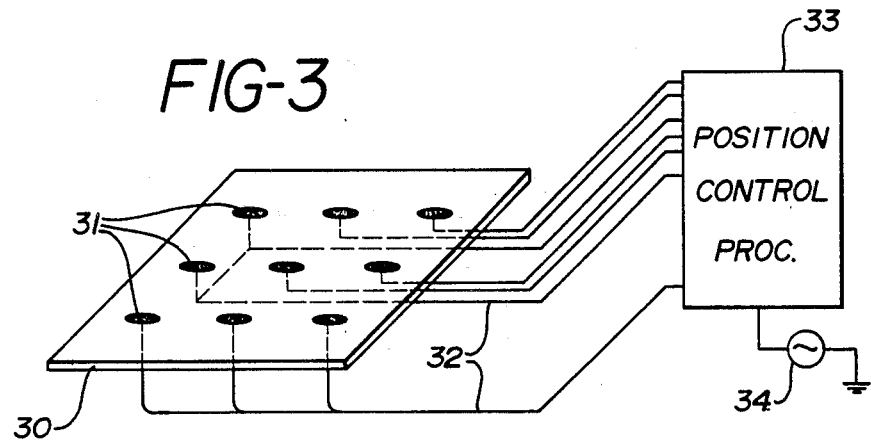
FIG. 3 graphically depicts an embodiment of the present invention.

As may be seen in FIG. 3, the grid points are preferably embedded in an insulating substrate 30 for careful maintenance of inter-grid point distance d (see also FIG. 1) as well as for providing a degree of physical integrity for repetitive use. Insulating substrate 30 may, in fact, be the walls of a container such as those found in the so-called microtiter type tray, or the bottom thereof, or in the case of the generalized cytometry instrument, any surface suitable for the illumination and detection of cells with that class of instruments.

The grid points 31 are ideally connected via connections 32 in any of a variety of ways, some examples of which are shown in FIG. 3, to a position control processor 33. The position control processor controls the grid point connections to alternating current source 34 in a manner appropriate for analysis.

For example, the position control processor may be programmed to provide cellular inter-grid point movement by sequential connection of grid points to the inhomogeneous field generating source whereby cells may follow preprogrammed routes. Thus, the cells may, for example, pass through specified environments containing test reagents or environments suitable for various testing methods. Additionally, the ability to selectively move the cells on a grid pattern, would enable an investigator to perform cell sorting based on cell kinetic response or other optically sensed cell characteristics. Since with the generalized cytometry instrument of Kamentsky, the location of the cells and the history of each cell is stored in the central processing unit or computer, one can de-energize the grid points or conducting contact areas having unwanted cells associated therewith, wash the system and perform a second set of analytical procedures on the remaining selected cell populations thereby effecting further subcell populations definitions. Similarly, undesired cells may be removed by translocating the cells past a sequentially energized series of grid points to a disposal area. Sorting based on the remaining cells utilizing such procedures may be performed on a repeated basis as necessary to achieve the desired level of purification and/or selection.

Upon achieving the final desired subset separation, the cells could be transported to adjacent grid systems for collection and for culturing. Indeed, further employment of the immobilizing surface of the present appartus is contemplated as a means whereby cells such as hybridomas and the like may be continuously cultured and their exuded products (antibodies in the case of hydridomas) facilely collected.

In conjunction with the class of generalized cytometry instruments described by Kamentsky, the present invention would permit automated cellular analysis and sorting to be continuously carried out for prolonged periods of time to obtain extremely sensitive sorting of particularly desired but rare cells in large heterogeneous populations. Accordingly, such a system would be vastly superior to the systems employing flow cytometric type cell sorters as those systems cannot be continuously operated for more than a few hours thereby limiting the utility of such systems as reagent preparative or investigational devices.

The invention can be used in still further applications and in particular, by appropriate selection of inter-grid point distance d, permits an investigator to bring cells into physical contact for studies of cell-to-cell communication. The grid points further permit the investigator to electronically pulse particular cells thereby stimulating pores to be open in the cell's membrane. The appearance of pores facilitates the transport of intracellular material betwen adjacent cells. If this process is carried to an extreme, actual cell fusion may result.

As may be readily apparent, the application of electronic pulses and the resultant formation of membrance pores will readily permit the introduction of biochemicals through the cell membrane. This operation of forced increased permeability may be programmed to be carried out at any stage of the cellular analysis or cell sorting process. Such a process would, for instance, permit the analysis of a cell for phenotypic determinants such as surface receptors or other markers, and then subsequently allow genotypic analysis through the introduction of nucleic acid probes such as those available from Enzo-Biochem of New York, N.Y. It should be noted that these probes need not be introduced together but may be introduced separately thereby allowing analysis to occur between the introduction of each probe. With the kinetic analysis properties of the generalized cytometry instrument of Kamentsky, it may be possible to actually track the time course genetic expression through the manufacture of messenger RNA and the subsequent appearance of gene products for each cell in an ensemble on the grid.

The shape and size of the grid containing the grid points may be adjusted to a virtually infinite number of embodiments. One useful embodiment, for example, would be the generation of a series of stripes of electronic grid points e.g. elongated contact areas arranged in a pattern, for use in that class of instruments employing synchronous detection. Alternatively, the grid points may be replaced with a series of finite repeating conducting bars, especially useful for the synchronous detection instruments. The cells would be introduced in suspension and then electrostatically immobilized on the bars.

Synchronous detectors derive their advantages from the repetitive detection of a pattern of cells via a lock-in amplifier to permit homogeneous testing and the extraction of a signal from a background or noise signal which may be much greater. This is accomplished by placing a rotating reticle in the image plane of the microscope with a pattern matching the image of the electrostatic bar pattern. Assuming the cells have been reacted with a probe (such as an antibody or nucleic acid probe) containing an optical label, rotating the reticle will provide an optical signal periodically transmitted through the reticle to a photomultiplier tube. The photomultiplier output would be synchronously detected by incorporating a reference signal from the rotating reticle. Thus, synchronous detection eliminates the need to wash free label from the ambient solution by suppressing any spatially uniform background optical signals. Further extensions of this embodiment would include a number of separate bar patterns on the microscope stage or other surface, each containing a separate cell sample undergoing analysis. A stage translator and method for detecting the optical register of the bar pattern in the reticle could be used to automatically interrogate each separate bar pattern over a predetermined time course for kinetic studies. These types of arrangements would permit the analysis of the average properties of cells rather than analyzing the cells on an individual basis.

If the patient sample is cellular in nature, it may be advantagous to transport the cells to each bar pattern location by utilizing the electrostatic grid technique. In this manner, samples can be automatically fed to the system and then removed following analysis. As with previously described preferred embodiments, traffic patterns in analysis results would be ideally computer controlled, such as by the position control processor.

EXPERIMENT 1—CELL MOTION—METHOD 1

Figure 4A:
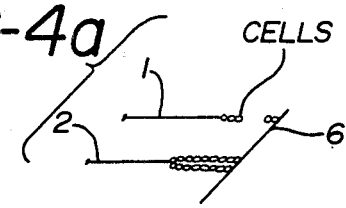
FIGS. 4 and 4a depict an embodiment of the present invention as used in Experiment 1.
Figure 4:
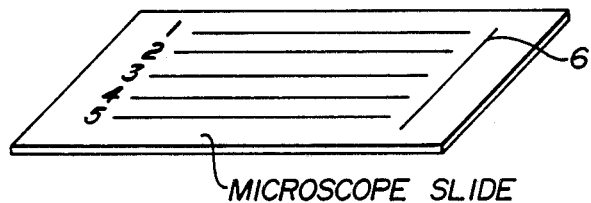

With reference to FIG. 4, 5 wires were glued to a microscope slide in parallel with all ends (the tips) aligned. Wire 6 was glued to the slide perpendicularly to the 5 wires and at one end of the parallel wires.

Wires 1–5 were left insulated except for the tips which were 200μ from wire 6. Wire 6 was entirely uninsulated. The ends of wires 1–5 were spaced 200μ apart. Wire 6 was grounded and wires 1–5 were left electrically floating. 2-1-14 (mouse myeloma) cells were washed twice in 300 mM Mannitol (Baker #2554-1) pH 7.5, conductivity ~8–10 μυ/cm, and resuspended to a concentration of $2 \times 10^6$ cells/ml. Cells were kept on ice until needed.

A drop (~100λ) of cell solution was placed on the uninsulated wire tips. In turn, each of the wires 1–5 was connected to a Tektronix signal generator (TM5006) [20 V peak-to-peak, 2 MHz sine wave] while the remaining wires were left unconnected.

The cells were seen to dielectrophorese to whichever wire was connected to the signal generator—See FIG. 4a which shows two circumstances of cellular alignment.

When wire #1 was disconnected, and wire #2 connected, the same configuration of aligned cells was seen at wire #2. After removal of signal to wire #1 the cells began to disperse gradually but slowly. Individual movement of cells is possible with this configuration when the cells are present at extremely low concentrations; on the order of $1 \times 10^3$ cells/ml. In some cases, the wires themselves presented a mechanical barrier to cell motion if the cells were initially positioned such that a "floating" wire was between them and the "active" wire. This can, of course, be obviated by placing the wire or contact within the surface.

EXPERIMENT 2—CELL MOTION—METHOD 2

The problem of wires presenting a physical impedance to cell movement was eliminated in a chamber constructed using a microscope slide upon which 8 copper conducting tape wire islands were applied in radial fashion, the outer most ends uniformly separated and forming the outline of a circle. 1 mil wire bonding aluminum wire was used to connect the islands and then covered with a ring of epoxy leaving the wire ends exposed for subsequent electrical connection as well as leaving exposed the wire islands crossing in the center of the epoxy ring.

Acid was used to etch away the wire islands in the center leaving a circular wall of epoxy having exposed, opposing point contacts. Distance across the center well between contacts was approximately 200μ.

2-1-14 (mouse myeloma) cells were washed twice in 200 mM Mannitol (Baler #2554-1) pH 7.5, conductivity 8–10 μυ/cm. Cells were resuspended to a concentration of $2 \times 10^6$ cells/ml in 300 mM Mannitol, and kept on ice until used.

A drop of cell solution was used to fill the chamber. In turn, each pair of opposing wire ends was connected to a "Viking Challenger" radio transmitter employed as a signal generator to create a 30 V peak-to-peak 2 MHz sinusoidal field across the chamber.

Cells migrated to the "active" point contacts and then to other pairs of point contacts as they were in turn connected to the signal generator. The cells aligned in a string of pearls fashion between the active point contacts. In this manner cells could be moved around the entire interior of the chamber. Directed movement of single cells can similarly be accomplished at cell concentrations on the order of $<1 \times 10^3$ cells/ml.

EXPERIMENT 3—MAINTAINING CELL LOCATION

In many applications actual cell testing or interrogation cannot be accomplished in the non-ionic or low conductivity solutions otherwise necessary to create the electrical cell locating fields. (It will readily be understood that although electric fields may be generated in high ionic solutions, such fields are accompanied by disadvantageous joule heating effects detrimental to continued cellular viability). Accordingly, the following demonstrates how cells may be located using the principles of the present invention and then, how their location can be maintained in the absence of an electric field using agarose. Thereafter, the agarose, on a suitable heating stage, may be melted at low temperature, either entirely or only at a specified location to allow repositioning of the cells via a subsequently applied electric field. 653 (mouse myeloma) cells were washed twice in a solution of 300 mM Mannitol (Baker Reagent Cat. #2554-1) pH 7.5 having a conductivity of 8–10 μυ/cm. The cells were then resuspended in 300 mM Mannitol to a concentration of $2 \times 10^6$ cells/ml. The final cell suspension was essentially ion free and therefore not subject to deleterious joule heating effects when placed in an alternating electric field of sufficiently high frequency. The cells were kept on ice until used.

Agarose type VII (Sigma #A-4018) was dissolved in 300 mM Mannitol to a 1% solution. The solution was then microwaved for 30 seconds to completely dissolve all the agarose and then kept warm in a boiling water bath until needed.

The heating stage was warmed to 30° C. and a small volume (about 100λ) of cell solution was placed between parallel electrodes glued to the bottom of a 60 mm Petri dish. Distance between the electrode wires was 200μ.

A 10 volt (peak-to-peak) 2 MHz (sine) field was then applied across the electrodes with a Tektronix TM5006 signal generator. This field caused cells to align themselves along field lines (perpendicular to the electrode wires) in pearl chain type arrangements such as those shown in FIG. 4a. Cells were in mutual contact.

The 1% agarose solution was then cooled to <37° C. and layered over the aligned cells. Addition of the agarose resulted in rotation of about half of the cells on an axis normal to the field lines. Rotating cells and adjacent cells were no longer in cellular contact. This effect could be totally eliminated by decreasing the field frequency to 1 MHz. By lowering the temperature to 27.5° C., the agarose gels immobilized the cells in the pearl chain arrangements, thereby permitting removal of the electric field without disruption of the cellular arrangement.

If the cells were permitted to rotate thereby creating intracellular spaces, the spaces could also be maintained upon solidification of the agarose. Reheating the solution to 31° C. melted the agarose sufficiently to allow cell repositioning via an applied electric field. By lowering the temperature to 27.5° C., the agarose was again solidified and cell position again maintained.

Standard commercial agarose can be remelted at 31° C. at least twice without requiring cell-destructive heat levels. Thereafter, it is theorized, the agarose becomes increasingly cross-linked requiring greater heat before melting is accomplished. However, this cross-linking effect can be reduced and the agarose "remelting-life" extended by limiting the formation of cross-linkages in manners well known by those skilled in the art.

The maintenance of intracellular space may be advantageous in some applications requiring optical interrogation of the cells. For those applications not requiring the intracellular space, it can be readily eliminated by application of lower field frequencies as aforesaid.

It will be readily apparent to those skilled in the art that numerous alternatives are possible without departing from either the spirit or the scope of the present invention.

What is claimed is:

1. An apparatus for immobilizing biological cells comprising:
    (a) an insulating substrate having a plurality of conducting contact areas mounted thereon;
    (b) an alternating current source having two outputs, one of said outputs connected to ground; and
    (c) connecting means for coupling the other of said current source outputs to said contact areas whereby a nonuniform electric field is produced emanating from said plurality of contact areas and capable of attracting and holding biological cells suspended in a conducting solution in contact with said plurality of contact areas, said connecting means further comprising means for controlling the connection between said contact areas and said current source whereby said cells may be released from said contact areas and, wherein said means for controlling includes means for disconnecting at least one contact area, independent of other contact areas, from said alternating current source whereby at least one predetermined cell at said one contact area may be selectively released from said one contact area while cells at other contact areas remain immobilized.

2. The apparatus as described in claim 1 further comprising electronic means for stimulating whereby at least one contact area may be separately stimulated for altering cellular characteristics of a cell associated with said stimulated contact area.

3. The apparatus as described in claim 1 wherein said contact areas are elongated and arranged in a pattern.

4. A method for immobilizing biological cells for subsequent testing or culturing comprising the steps of:
    (a) providing the biological cells to be immobilized in a solution capable of supporting an inhomogeneous electric field and maintaining cellular viability for a time at least sufficient to conduct the desired testing or culturing of said cells; and
    (b) bringing said biological cells in contact with an apparatus comprising:
        (i) an insulating substrate having a plurality of conducting contact areas mounted thereon;
        (ii) an alternating current source having two outputs, one of said outputs connected to ground; and
        (iii) connecting means for coupling the other of said current source outputs to said contact areas whereby a nonuniform electric field is produced emanating from said plurality of contact areas and capable of attracting and holding biological cells suspended in a conducting solution in contact with said plurality of contact areas, wherein said connecting means coupling said current source to said contact area further comprises control means for independently connecting said current source to said contact areas;
    (c) energizing said current source connected to said contact areas for creating an inhomogeneous electric field whereby said biological cells are immobilized on said contact areas.

5. The method of claim 4 wherein said energizing step further includes the step of directing cellular movement between contact areas.

* * * * *